(12) United States Patent
Mouton

(10) Patent No.: US 9,271,877 B2
(45) Date of Patent: Mar. 1, 2016

(54) COMBINED COMPRESSION AND ABSORPTION DRESSING/BANDAGE

(75) Inventor: Johannes Petrus Mouton, Centurion (ZA)

(73) Assignee: IWMT Intellectual Property Holdings (PTY) LTD. (ZA)

( * ) Notice: Subject to any disclaimer, the term of this patent is extended or adjusted under 35 U.S.C. 154(b) by 505 days.

(21) Appl. No.: 13/696,495

(22) PCT Filed: May 9, 2011

(86) PCT No.: PCT/IB2011/052034
§ 371 (c)(1),
(2), (4) Date: Nov. 6, 2012

(87) PCT Pub. No.: WO2011/138771
PCT Pub. Date: Nov. 10, 2011

(65) Prior Publication Data
US 2013/0060217 A1    Mar. 7, 2013

(30) Foreign Application Priority Data

May 7, 2010    (ZA) ...................................... 10/3269

(51) Int. Cl.
*A61F 13/00* (2006.01)
*A61F 13/06* (2006.01)
*A61F 13/08* (2006.01)
*A61F 13/02* (2006.01)

(52) U.S. Cl.
CPC ........... *A61F 13/069* (2013.01); *A61F 13/0206* (2013.01); *A61F 13/08* (2013.01); *A61F 13/085* (2013.01); *A61F 2013/0028* (2013.01); *A61F 2013/00102* (2013.01); *A61F 2013/00119* (2013.01); *A61F 2013/00157* (2013.01); *A61F 2013/00238* (2013.01); *A61F 2013/00519* (2013.01); *A61F 2013/00604* (2013.01); *A61F 2013/00744* (2013.01)

(58) Field of Classification Search
CPC ... A61F 13/0206; A61F 13/069; A61F 13/08; A61F 2013/00119; A61F 2013/00238; A61F 2013/00604
USPC ..................................... 604/358, 372; 602/41
See application file for complete search history.

(56) References Cited

U.S. PATENT DOCUMENTS

| | | | | | |
|---|---|---|---|---|---|
| 4,349,020 | A | * | 9/1982 | Krikorian | ......... A61F 13/00038 602/75 |
| 4,813,944 | A | * | 3/1989 | Haney et al. | ................... 604/358 |
| 6,120,539 | A | * | 9/2000 | Eldridge | ............... A61F 2/0063 600/37 |
| 7,112,712 | B1 | * | 9/2006 | Ancell | ........................... 602/41 |

(Continued)

OTHER PUBLICATIONS

International Search Report and Written Opinion dated Oct. 21, 2011 issued in PCT Patent Application No. PCT/IB11/52034, 11 pages.

*Primary Examiner* — Michele M Kidwell
(74) *Attorney, Agent, or Firm* — Grossman Tucker Perreault & Pfleger PLLC

(57) ABSTRACT

A combined compression and absorption dressing/bandage, which includes a short stretch compression bandage and at least one absorptive wound dressing comprising at least one absorbent layer of a non-woven fabric of any one or more of cotton, viscose and polyester fibers, the absorbent layer having an operative inner face and an operative outer face, the at least one wound dressing being bonded to the short stretch compression bandage with its inner face towards the bandage and the outer face facing away from the bandage.

18 Claims, 2 Drawing Sheets

(56) References Cited

U.S. PATENT DOCUMENTS

Figure 1:
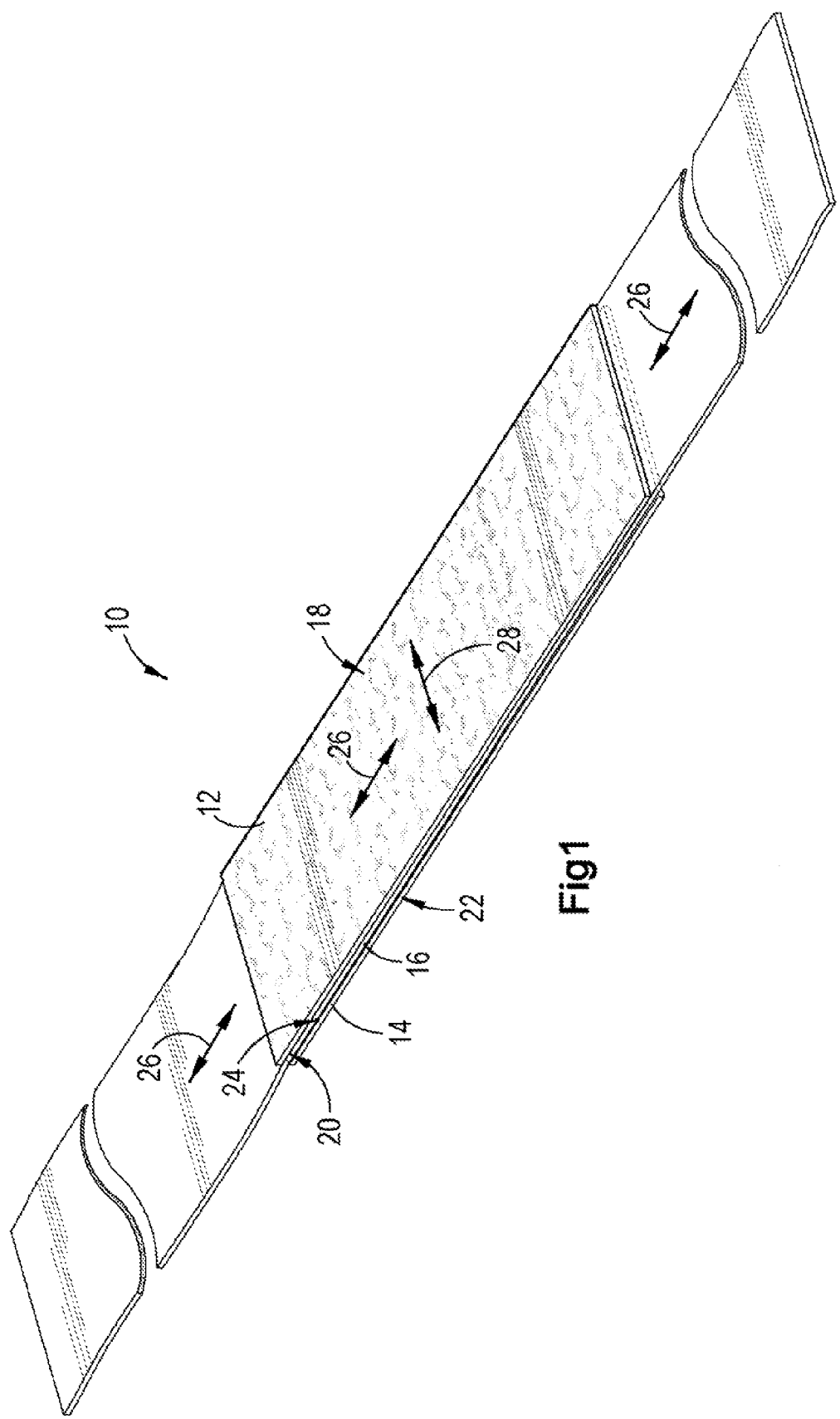

| | | | |
|---|---|---|---|
| 8,206,632 B2 * | 6/2012 | Rousseau | A61L 27/40 156/308.6 |
| 8,403,873 B2 * | 3/2013 | Schuren | A61F 13/069 602/53 |
| 2005/0084647 A1 * | 4/2005 | Menzies et al. | 428/99 |
| 2009/0112145 A1 * | 4/2009 | Lecomte et al. | 602/76 |

* cited by examiner

COMBINED COMPRESSION AND ABSORPTION DRESSING/BANDAGE

CROSS REFERENCE TO RELATED APPLICATIONS

This application claims priority to International PCT Application No. PCT/IB2011/052034 filed May 9, 2011, which claims priority to South African Application No. 2010/03269 filed May 7, 2010, the entire content of each of which are fully incorporated herein by reference This invention relates to a combined compression and absorption dressing/bandage. It relates also to a method of manufacturing a combined compression and absorption dressing/bandage, and to a method of treating a wound.

BACKGROUND OF THE INVENTION

The inventor is aware of compression bandages used in combination with wound dressings to care for wounds by exerting compression on the wounds, whilst absorbing moisture from a wound.

SUMMARY OF THE INVENTION

Broadly according to one aspect of the invention, there is provided a combined compression and absorption dressing/bandage, which includes a short stretch compression bandage; and an absorptive wound dressing integral with at least a portion of the compression bandage.

According to another aspect of the invention, there is provided a combined compression and absorption dressing/bandage, which includes a short stretch compression bandage; and at least one wound dressing comprising at least one absorbent layer of a non-woven fabric made up of cotton and viscose and polyester fibres, the absorbent layer having an operative inner face and an operative outer face, the at least one wound dressing being bonded to the short stretch compression bandage with its inner face towards the bandage and the outer face facing away from the bandage.

The combined compression and absorption dressing/bandage may include two absorbent outer layers of any one of non-woven viscose and cotton and polyester fibres and a short stretch compression bandage inner layer.

The short stretch compression bandage may be of a polyester knit of 50 g/m² to 150 g/m². In particular the short stretch compression bandage may be of a polyester knit of about 70 g/m².

The short stretch compression bandage may be of a non-absorbent material that can stretch and that could adsorb liquids.

The inner layer may be of a polyester knit scrim sandwiched between the two outer layers.

The inner layer may have a yarn count of 30 threads/cm² to 50 threads/cm². In particular, the inner layer may have a yarn count of about 40 threads/cm².

The inner layer may be of 100% polyester.

The two absorbent outer layers may each have a weight per unit area of 70 g/m² to 200 g/m².

The absorbent outer layers may be in the form of needle punched fibre batts or webs. The outer layers may comprise 60% to 80% viscose fibres by mass and 20% to 40% polyester fibres by mass. In particular, the outer layers may comprise about 70% viscose fibres by mass and about 30% polyester fibres by mass.

The fibre in the outer layers may have a fibre titre of 1.0 to 5 denier. The outer layers may have been subjected to a thermal treatment process to provide the outer layers with a substantially smooth outer surface.

The absorbent outer layers and the short stretch inner layer may be bonded together by means of a needle punching process with a needle punching density of between 200 punches/cm² to 700 punches/cm².

The outer layers and the short stretch inner layer may be bonded together by means of a needle punching process with a needle punching density of about 430 punches/cm².

The combined compression and absorption dressing/bandage may have a thickness of between 1.5 mm and 3 mm. In particular, the compression bandage may have a thickness of about 2 mm.

The combined compression and absorption dressing/bandage may have a weight per unit area of between 200 g/m² to 500 g/m². In particular, the compression dressing/bandage may have a weight per unit area of about 270 g/m².

The combined compression and absorption dressing/bandage may have length of about 0.5 m to 4 m and a width of about 75 mm to 100 mm.

The wound-dressing portion of the compression dressing/bandage may have a length of between 0.5 m to 2 m and a width corresponding with the width of the compression dressing/bandage.

The wound-dressing portion of the compression dressing/bandage may have a length of about 1.3 m.

Advantageously, the compression dressing/bandage may be used with either one of its operatively outer faces towards or in contact with the wound.

Broadly according to another aspect of the invention, there is provided a method of manufacturing a short stretch compression/dressing, which includes manufacturing at least one needle-punched fibre bat of viscose and polyester by means of a needle loom, the at least one bat having an operative inner and outer face;

sandwiching a layer of short stretch polyester knit onto the at least one fibre batt with its operatively inner face towards a layer of short stretch polyester knit by means of a needle-punching process to form a layered short stretch laminated pad.

More particularly there is provided a method of manufacturing a short stretch compression/dressing, which includes manufacturing at least two needle-punched fibre bats of any one of viscose, cotton and polyester by means of a needle loom, each bat having an operative inner and outer face;

sandwiching at least one layer of short stretch polyester knit between the at least two fibre batts with their operatively inner faces in face-to-face relationship towards the at least one layer of short stretch polyester knit by means of a needle-punching process to form a layered short stretch laminated pad.

The at least one short stretch inner layer may be sandwiched by being bonded together by means of a needle punching process with a needle punching density of between 200 punches/cm² to 700 punches/cm². In particular, the outer layers and the short stretch inner layer may be bonded together by means of a needle punching process with a needle punching density of about 430 punches/cm².

The invention extends to a method of treating a wound, which method includes bandaging the wound by making use of a combined compression and absorption dressing/bandage as describe above.

The invention is now described, by way of a non-limiting example, with reference to the accompanying diagrammatic drawings.

DRAWING(S)

Figure 2:
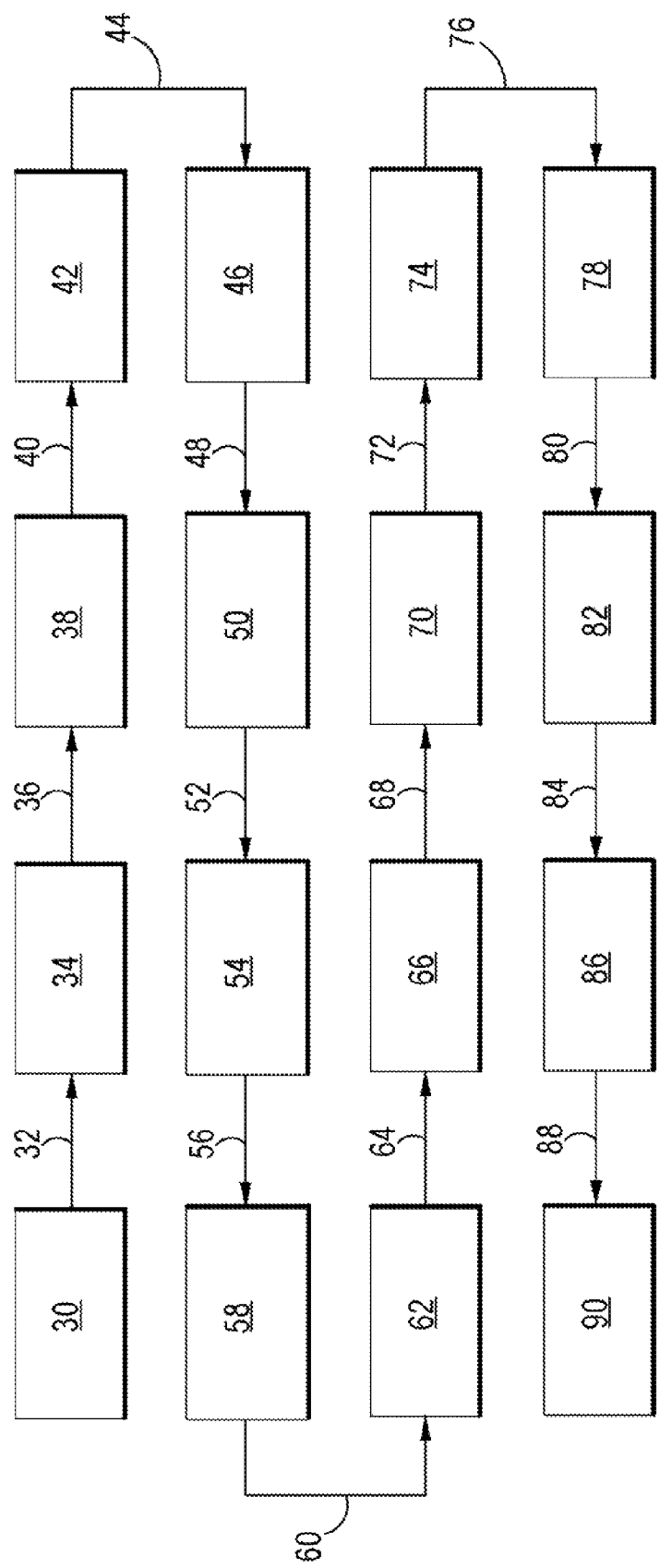

In the drawings:

FIG. 1 shows, schematically, a three dimensional view of a compression dressing/bandage in accordance with the invention; and FIG. 2 shows, schematically, a flow-diagram of steps forming part of the method of making a dressing/bandage in accordance with the invention.

EMBODIMENT OF THE INVENTION

With reference to FIG. 1 of the drawings, a dressing/bandage in accordance with the invention is generally designated by reference numeral 10. For clarity, the thickness of the wound dressing 10 is exaggerated in FIG. 2. The wound dressing 10 is in the form of a rectangular laminate pad which comprises first and second absorbent layers 12, 14 and an inner layer 16 sandwiched between and bonded to the first and second absorbent layers 12, 14. The three layers 12, 14, 16 are bonded together by means of a needle-punching process as hereinafter described in further detail.

Each of the first and second absorbent layers 12, 14 is of a non-woven fabric comprising about 70% viscose fibres by volume and about 30% polyester fibres by volume. The viscose fibres and polyester fibres are porous fibres having a length of about 3 mm to 10 mm and a fineness of 2-2.5 denier. Further, each of the first and second absorbent layers 12, 14 have a weight per unit area of about 100 g/m$^2$.

The inner layer 16 is in the form of 100% polyester short stretch weft knit scrim with a yarn count of 40 and a weight of 70 g/m$^2$.

The wound dressing 10 thus has a total weight per unit area of about 270 g/m$^2$, and has a total thickness of about 1.5 mm-2.5 mm.

In particular, each of the first and second absorbent layers 12, 14 is in the form of a fibre batt or mat. The first absorbent layer 12 has an operatively outer face 18 and an operatively inner face 20, and the second absorbent layer 14 has an operatively outer face 22 and an operatively inner face 24. The first and second absorbent layers 12, 14 are oriented such that their operatively inner faces 20, 24 are in face-to-face relationship, with the inner layer 16 thus being in contact with the operatively inner faces 20, 24 of the first and second absorbent layers 12, 14. The three layers 12, 14, 16 together form a three-layered laminate pad or body.

As mentioned above, the first and second absorbent layers 12, 14 and the inner layer 16 are bonded together by means of a needle-punching process, the needle punching density of the needle-punching process effecting such bonding together of the layers 12, 14, 16 being about 300-500 punches/cm$^2$. Further, the operatively outer layers 18, 22 of the first and second absorbent layers 12, 14 have been subjected to heat treatment, such that the wound dressing 10 is provided with substantially smooth and non-adherent outer faces, as will become more apparent hereinafter when manufacturing of the wound dressing 10 is described in more detail.

Importantly, the inner layer 16 is of a short stretch compression bandage. The bandage can stretch in the direction of arrows 26 but not in the direction of arrow 28.

The compression dressing/bandage 16 can be supplied in lengths of 2 m to 4 m and widths of 75 mm to 100 mm. The dimensions of the outer layers 12, 14 are matched to the width of the bandage 16. The outer layers 12, 14 run along the first 1.3 m of the dressing/bandage, where after a length of about 1.5 m to 2 m defines a normal stretch bandage.

FIG. 2 shows a flow diagram of steps employed in a method of making a compression dressing/bandage in accordance with the invention. In this figure, block 30 represents a blending process during which the 70% viscose fibres and 30% polyester fibres from which each of the absorbent layers 12, 14 are manufactured, are blended. The blended fibres are then moved along a notional flow line 32 to a size-reduction process represented by block 34, during which size-reduction process the size of blended fibre tufts are reduced. After the size reduction, the fibre tufts are moved along a notional flow line 36 to a carding process, represented by block 38, during which carding process the fibres are combed and disentangled, to arrange them in to a fibrous web having more or less parallel fibres. After carding, the fibrous web is moved along a notional flow line 40 to a cross-lapping process, represented by block 42. During the cross-lapping process, the fibrous web is build up, by layering, to the desired finished non-woven weight. After cross-lapping, the fibrous web is moved along a notional flow line 44 to a needleloom where needle-punching takes place, to bond the fibres of the web together.

In this example, the fibrous web from which each of the absorbent layers 12, 14 is formed undergoes four needle-punching runs, the various needle-punching runs being notionally represented by blocks 46, 50, 54 and 58. Thus, the fibrous web passes through four needle boards. In this example, the needleloom employed to effect the needle-punching is a felting loom having four needle boards, so that the fibrous web is fed through the needleloom once only. Flow lines 48, 52 and 56 notionally represent movement of the fibrous web respectively from the needle-punching run 46 to the needle-punching run 50, from the needle-punching run 50 to the needle-punching run 54, and from the needle-punching run 54 to the needle-punching run 58.

Each of the needle boards of the needle loom is 0.25 m wide and 1 m long, and has 4,000 needles mounted thereon. Thus, each needle board has 16,000 needles/linear meter. Each of the needles has a diameter of 0.58 mm, has a taper- or conical point and has 9 barbs. The fibrous web is fed through the needleloom at a feed rate of 3 m/minute, and the punching frequency of each needle board is 800-1,000 punches/minute. A punching density of between 300 and 500 punches/cm$^2$, depending on the punching frequency, is thus obtained during each of the needle-punching runs 46, 50, 54, 58. The fibrous web exposed to the needle-punching runs 46, 50, 54, 58 thus yields a fibrous batt or mat which has been exposed to a total needle-punching density of between about 1,200 and 2000 punches/cm$^2$.

During the first needle-punching run 46, the depth to which the needles penetrate the fibrous web is about 5.4 mm, during the second needle-punching run 50 the depth of needle penetration is about 4.6 mm, during the third needle-punching run 54 the depth of needle penetration is about 4.3 mm, and during the fourth and final needle-punching run 58 the depth of needle penetration is about 3.2 mm.

As mentioned above, once the fibrous web has been exposed to the aforedescribed needle-punching process, a fibrous batt or mat is formed. Said fibrous batt is then, if required, moved along a notional flow line 60 to a chemical treatment process, represented by block 62, where the fibrous batt can be chemically treated. After said chemical treatment of the batt, one major face of the fibrous batt, which face is intended to form one of the operatively outer faces 18, 22 of the first and second absorbent layers 12, 14, is then exposed to a heat treatment process to provide said outer face of the fibrous mat with a smooth, relatively non-fluffed and non-adherent surface. Movement of the fibrous web from the chemical treatment process 62 to the heat treatment process is indicated by notional flow line 64, the heat treatment process being represented by block 66. If chemical treatment of the fibrous batt is not required, as is the case with the present example, it is moved directly from the needle-punching run 58 to the heat treatment process 66. Subsequent to the aforedescribed heat treatment, the fibrous batt is then moved along a notional flow line 68 to a winding and cutting process, represented by block 70, where the batt is cut into the required width and is wound onto a roller.

Referring back to the flow diagram of FIG. 2, a notional flow line 72 represents movement of two rolls of manufactured fibrous batt to a layering process, represented by block 74, where the short stretch bandage 16 is sandwiched between the first and second absorbent layers 12, 14, each of which is in the form of the aforedescribed fibrous batt. In particular, the fibrous batts or absorbent layers 12, 14 are oriented such that their smoothened faces or surfaces, i.e. those faces or surfaces which underwent heat treatment, face operatively outwardly. After sandwiching of the three layers 12, 14, 16, the layers are moved along a notional flow line 76 to a needleloom which effects a bonding needle-punching process or run, represented by block 78. The needleloom used for the bonding needle-punching process or run 78 is a loom having a single needle board. The three layers are thus bonded together by means of the needle-punching run represented by block 78. During this bonding needle-punching run 78, the feed rate, the type of and number of needles mounted on the needle board and the dimensions of the needle board used is the same as that used during the needle-punching runs 46, 50, 54, 58. During the bonding needle-punching run 78, the punching frequency of the needle board is such that a bonding punching density of about 300-350 punches/cm$^2$ is obtained. After the bonding needle-punching run 78, a sheet, which is in the form of a three-layered laminate pad, is thus yielded. The laminate pad or sheet is then moved along a notional flow line 80 to a cutting process, indicated by block 82, where it is cut to yield the required size wound dressings 10. After the wound dressings 10 have been cut to the required size, they are moved along a notional flow line 84 to a packing station 86, where they are packaged, typically separately packaged into airtight packages. The packaged wound dressings are then moved along a notional flow line to a sterilization process, represented by a block 90, where the packaged wound dressings are sterilized in conventional fashion.

Naturally, the aforedescribed steps for making a wound dressing in accordance with the invention need not all be executed on the same production line. In fact, all the steps need not even be executed at the same location or manufacturing plant.

Although the method, as far as manufacturing of the first and second absorbent layers 12, 14 are concerned, is hereinbefore described with reference to a needleloom which includes four needle boards, it is to be appreciated that a needle loom having a single needle board can also advantageously be applied, in which case the fibrous web will be fed four times through the needle loom.

By employing the method and raw materials as hereinbefore described, a compression dressing/bandage having a thickness of about 1.5 mm-2.5 mm is obtained.

The invention as described and illustrated provides a compression dressing/bandage which can be used to dress a wide spectrum of wounds to limbs and combines the effects of a wound dressing and a compression bandage used in combination. The absorbent layers, being stretchable in unison with the short stretch bandage provides a comfortable fit and permit long term treatment of wounds to limbs.

The porous viscose fibres have high moisture absorbing properties and are air-permeable. In turn, polyester fibres are relatively tough and strong and have high abrasion resistance. In addition, polyester fibres have the ability after heat treatment, to retain a smoothened or flattened profile. Because of the combination of viscose and polyester fibres of the absorbent layers 12, 14 of the present compression dressing/bandage, each of the outer layers 12, 14, whilst being air-permeable, has exceptional moisture absorbing properties, thus yielding a relatively tough and strong compression dressing/bandage with high moisture absorbing properties. Further, because of the softness of porous viscose fibres, the wound dressing 10 is relatively soft and thus resists discomfort to a patient whose wound is dressed by a wound dressing in accordance with the invention.

The wound dressing in accordance with the invention, by virtue of its particular construction and the way in which it is manufactured, is known not only to absorb exudate from wounds, but also, because of capillary action stemming from the construction of the dressing, to direct absorbed exudates and bacteria away from a wound. Further, the wound dressing in accordance with the invention, because of said capillary action, has the ability to "kick-start" wounds that are classified as unresponsive or dead wounds, i.e. wounds which do not exude moist or liquids. Furthermore, the wound dressing has the ability to retain absorbed exudate, such that absorbed moist does not leak or drip there from. The particular invention described herein has the added advantage of compression treatment related to improved blood and lymph circulation.

Furthermore, because both the outer surfaces of the compression dressing/bandage 10 are smoothened by the aforedescribed heat treatment process, the dressing is non-directional, i.e. it can be used with either of its faces in contact with a wound. Because the outer surfaces of the wound dressing are relatively non-adherent, the dressing in accordance with the invention can comfortably be used with ointment employed in treatment of wounds.

The invention as described and illustrated thus provides a compression dressing/bandage which not only has good absorption qualities, but also serves to improve blood and lymph circulation in the region of the wound. This is of particular importance where wounds are related to associated circulatory conditions such as lymphodemia and other wounds such as ulcers and burn wounds.

What is claimed is:

1. A combined compression and absorption dressing/bandage, which includes
    an inner layer sandwiched between a first outer layer and a second outer layer;
  wherein:
    the inner layer is a short stretch compression bandage comprising a knit scrim;
    the first outer layer comprises a first absorptive wound dressing that is in direct contact with a first surface of the inner layer, the first absorptive wound dressing comprising at least one first absorbent layer having a first operative inner surface and a first operative outer surface;
    the second outer layer comprises a second absorptive wound dressing that is direct contact with a second surface of the inner layer, the second absorptive wound dressing comprising at least one second absorbent layer having a second operative inner surface and a second operative outer surface;
    the first and second absorbent layers each comprise a nonwoven fabric of any one or more of cotton, viscose and polyester fibres;

the first operative inner surface is in direct contact with the first surface of the inner layer;

the second operative inner surface is in direct contact with the second surface of the inner layer; and the first and second outer surfaces face away from the inner layer.

2. A combined compression and absorption dressing/bandage as claimed in claim 1, wherein the first and second absorbent layers are of non-woven viscose and polyester fibres.

3. A combined compression and absorption dressing/bandage as claimed in claim 1, wherein said knit scrim is a polyester knit with a weight per unit area of 50 g/m$^2$ to 150 g/m$^2$.

4. A combined compression and absorption dressing/bandage as claimed in claim 1, wherein the inner layer is of a non-absorbent material that can stretch and that could adsorb liquids.

5. A combined compression and absorption dressing/bandage as claimed in claim 2, wherein said knit scrim is a polyester knit scrim.

6. A combined compression and absorption dressing/bandage as claimed in claim 5, wherein the inner layer has a yarn count of 30 threads/cm$^2$ to 50 threads/cm$^2$.

7. A combined compression and absorption dressing/bandage as claimed in claim 2, wherein the inner layer is of 100% polyester.

8. A combined compression and absorption dressing/bandage as claimed in claim 2, wherein the first and second outer layers each have a weight per unit area of 70 g/m$^2$ to 200 g/m$^2$.

9. A combined compression and absorption dressing/bandage as claimed in claim 2, wherein the first and second outer layers are each in the form of needle punched fibre batts or webs.

10. A combined compression and absorption dressing/bandage as claimed in claim 2, wherein the first and second outer layers each comprise 60% to 80% viscose fibres by mass and 20% to 40% polyester fibres by mass.

11. A combined compression and absorption dressing/bandage as claimed in claim 2, wherein the first and second outer layers each have a fibre titre of 1.0 to 5 denier.

12. A combined compression and absorption dressing/bandage as claimed in claim 2, wherein the first and second outer layers have each been subjected to a thermal treatment process to provide the outer layers with a substantially smooth outer surface.

13. A combined compression and absorption dressing/bandage as claimed in claim 2, wherein the first and second outer layers and the inner layer are bonded to one another by a needle punching process with a needle punching density of between 200 punches/cm$^2$ to 700 punches/cm$^2$.

14. A combined compression and absorption dressing/bandage as claimed in claim 1, wherein the compression and absorption dressing/bandage has a thickness of between 1.5 mm and 3 mm.

15. A combined compression and absorption dressing/bandage as claimed in claim 1, wherein the compression and absorption dressing/bandage has a weight per unit area of between 200 g/m$^2$ to 500 g/m$^2$.

16. A combined compression and absorption dressing/bandage as claimed in claim 1, wherein the compression and absorption bandage has a length of about 0.5 m to 4 m and a width of about 75 mm to 100 mm.

17. A combined compression and absorption dressing/bandage as claimed in claim 16, wherein first and second absorptive wound dressings each have a length of between 0.5 m to 2 m and a width corresponding with the width of the compression and absorption dressing/bandage.

18. A combined compression and absorption dressing/bandage as claimed in claim 17, wherein the first and second absorptive wound dressings each have a length of about 1.3 m.

\* \* \* \* \*